United States Patent
Ashby et al.

[11] Patent Number: 5,879,394
[45] Date of Patent: Mar. 9, 1999

[54] TIBIAL ELEMENT FOR A REPLACEMENT KNEE PROSTHESIS

[75] Inventors: Alan Ashby, Lymington, England; Paul F. Dorrell, Castleconnell, Ireland

[73] Assignee: Howmedica International Inc., Shannon, Ireland

[21] Appl. No.: 864,020

[22] Filed: May 27, 1997

[30] Foreign Application Priority Data

May 28, 1996 [GB] United Kingdom .................. 9611060

[51] Int. Cl.⁶ ........................................ A61F 2/38
[52] U.S. Cl. .............................................. 623/20
[58] Field of Search ............................... 623/20

[56] References Cited

U.S. PATENT DOCUMENTS

| | | | |
|---|---|---|---|
| 4,711,639 | 12/1987 | Grundei | 623/20 |
| 4,728,332 | 3/1988 | Albrektsson | 623/20 |
| 4,936,853 | 6/1990 | Fabian et al. | 623/20 |
| 5,071,438 | 12/1991 | Jones et al. | 623/20 |
| 5,282,868 | 2/1994 | Bahler | 623/20 |
| 5,326,361 | 7/1994 | Hollister | 623/20 |
| 5,344,461 | 9/1994 | Philipot | 623/20 |
| 5,395,401 | 3/1995 | Bahler | 623/20 |
| 5,405,396 | 4/1995 | Heldreth | 623/20 |
| 5,609,639 | 3/1997 | Walker | 623/20 |
| 5,658,342 | 8/1997 | Draganich | 623/20 |
| 5,683,468 | 11/1997 | Pappas | 623/20 |

FOREIGN PATENT DOCUMENTS

| | | | |
|---|---|---|---|
| 519873 | 12/1992 | European Pat. Off. | 623/20 |
| 2253147 | 9/1992 | United Kingdom | 623/20 |
| 2280375 | 2/1995 | United Kingdom . | |
| 2280376 | 2/1995 | United Kingdom . | |
| WO 9638103 | 12/1996 | WIPO . | |

*Primary Examiner*—Michael J. Milano
*Attorney, Agent, or Firm*—Peter C. Richardson; Lawrence C. Akers; Raymond W. Augustin

[57] ABSTRACT

A tibial element is provided for a replacement knee prosthesis which comprises a tibial tray provided with a bearing component having medial and lateral compartments. Control means acting between the tray and the bearing component are included which provide free posterior and anterior movement of the lateral compartment which is greater than any allowed free posterior and anterior movement of the medial compartment in relation to the tray. Thus, there is no relative free posterior movement and anterior movement of the medial compartment or some may be allowed.

14 Claims, 8 Drawing Sheets

TIBIAL ELEMENT FOR A REPLACEMENT KNEE PROSTHESIS

BACKGROUND OF THE INVENTION

1. Field of the Invention

This invention relates to a tibial element for a replacement knee prosthesis of the kind comprising a tibial tray provided with a bearing component having medial and lateral compartments.

2. Description of the Prior Art

Reconstruction of the painful arthritic knee is now a commonplace operation throughout the world with results reported to be of similar success to hip replacements. However, some significant problems relating to knee surgery remain. Among these are wear and damage of articulating surfaces, and repeatability and ease of achieving a stable balanced reconstruction.

In recent years there has been a return to the original concepts of more conforming and constrained knee replacements (i.e., Total Condylar) since concerns as to the long term survivorship of "flat" bearing forms have been raised. Greater congruency between metal and plastic components leads to larger contact areas which are believed to reduce the stresses transmitted to the plastic material. High stress levels are believed to initiate microscopic cracks within the plastic leading to the long term breakdown of the material or wear. Therefore, any reduction in the stress experienced by the plastic is beneficial. However, with increased conformity comes the risk of reduced range of motion from over-constraint and tibial fixation concerns with unloading of the soft tissue structures.

The advent of sliding Meniscal devices sought to combine increased tibiofemoral congruency while restoring normal joint function by allowing the tibial insert to move relative to the base plate.

There are now various meniscal systems available on the market, some with good long-term success, for example as set out in:

Pappas M J, Buechel F F

The New Jersey Low-Contact-Stress Knee Replacement System:

Biomechanical Rationale and Review of the First 123 Cemented Cases.

(Rrch Orthop Trauma Surg 1986; 105: 197–204)

Goodfellow J W, O'Connor J

Clinical Results of the Oxford Knee.

(Clin. Orthop. 1986; 205: 21–42)

However, problems with this type of device have also been reported in the form of insert dislocation and fracture.

SUMMARY OF THE INVENTION

The object of the present invention is to overcome some of the difficulties referred to above.

According to the present invention a tibial element for a replacement knee prosthesis comprises a tibial tray provided with a bearing component having medial and lateral compartments and including control means acting between the tray and the bearing component which provide free posterior and anterior movement of the lateral compartment which is greater than any allowed free posterior and anterior movement of the medial compartment in relation to the tray.

Thus, there may be no relative free posterior movement and anterior movement of the medial compartment or some may be allowed.

The control means acting between the tray and the bearing compartment may allow free rotational movement of said lateral compartment in relation to the tray about a pivotal axis centered within the medial compartment.

With this arrangement the control means may also be constructed to act to allow restricted anterior and posterior movement of the pivotal axis.

With the rotation centered within the medial compartment there is a mimicking of the natural knee physiology. The articulation of the bearing component ensures high conformity with the femoral condyles within the walking cycle and full conformity with the tibial base plate at all times. The center of rotation being within the medial compartment ensures that the more heavily loaded condyle is always fully supported by the tibial tray thereby eliminating the chance of the bearing component tipping, dislocating or jamming on the edge of the tray.

The invention, for the provision of the asymmetric movement, is intended to provide good post-operative stability of the joint, provide a low sensitivity to surgical technique and soft tissue quality and provide mechanisms to avoid the likelihood of insert dislocation and other bearing damage.

In a preferred construction the tray is standard for both left and right knees and the bearing components are handed.

With this arrangement the tray can be substantially symmetrical about a vertical axis.

The medial compartment being less mobile than the lateral compartment, the medial side can be made larger than the lateral compartment so that the lateral compartment avoids soft tissue impingement during its greater degree of travel.

In a convenient construction, the control means includes a curved track in the base of the bearing component and the control means can include a guide located within the track and carried on the tray.

With this construction the guide can be in the form of a projecting boss.

The guide can be provided by part of fastening means which act to secure an attachment element, for example a stem, to the lower part of the tray.

The guide may also provide means for securing the bearing component to the tray, thus in a preferred construction the bearing component is a resilient snap fit onto the guide.

Preferably, the means for securing the bearing component to the tray are independently operable and can be releasable.

The control means can also include a control abutment located within the track preferably posteriorly of the guide.

This control abutment can be made integral with the tibial tray.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
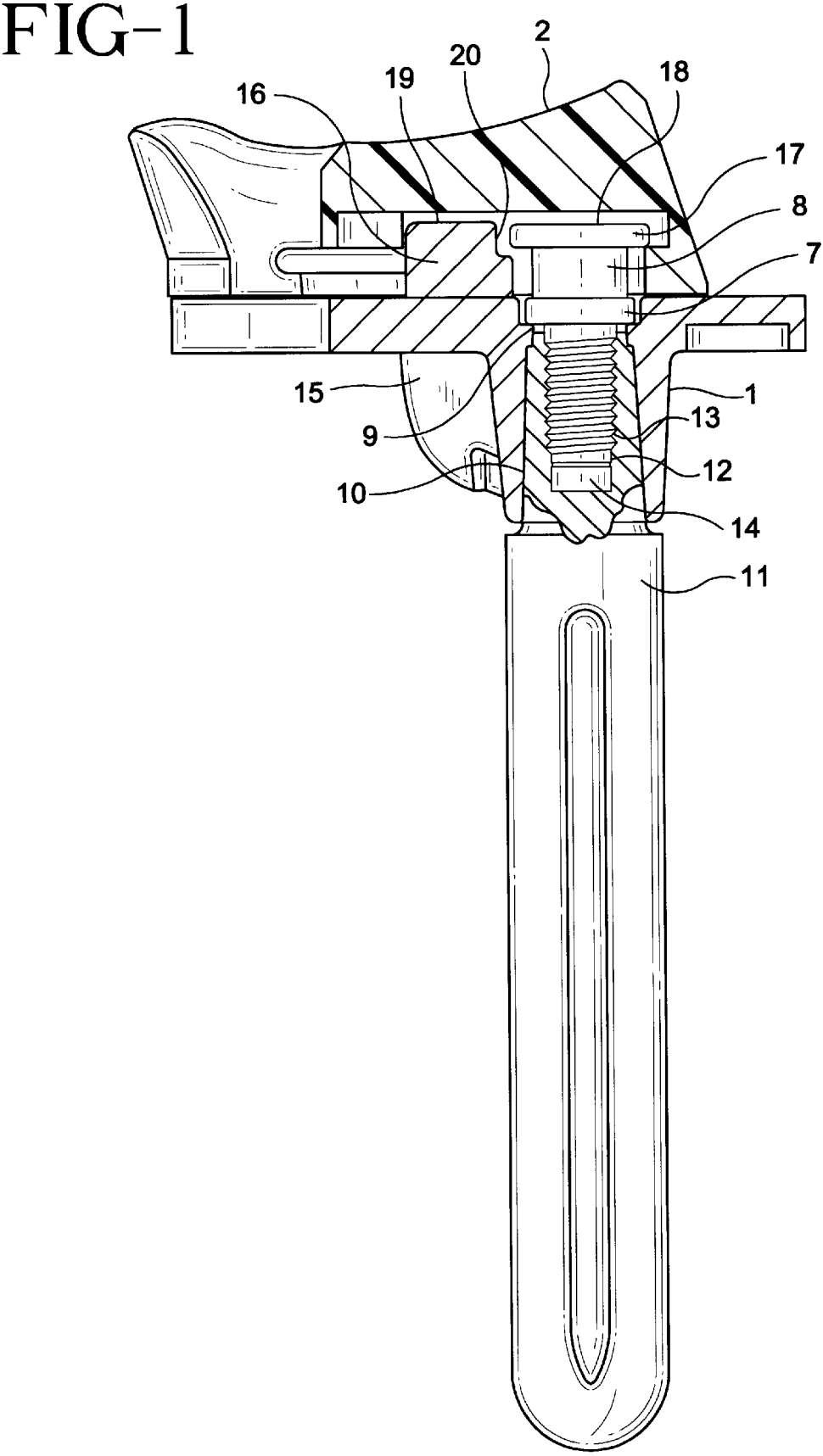
FIG. 1 is a part cross-sectional side elevation of a tibial element according to the present invention.
Figure 2:
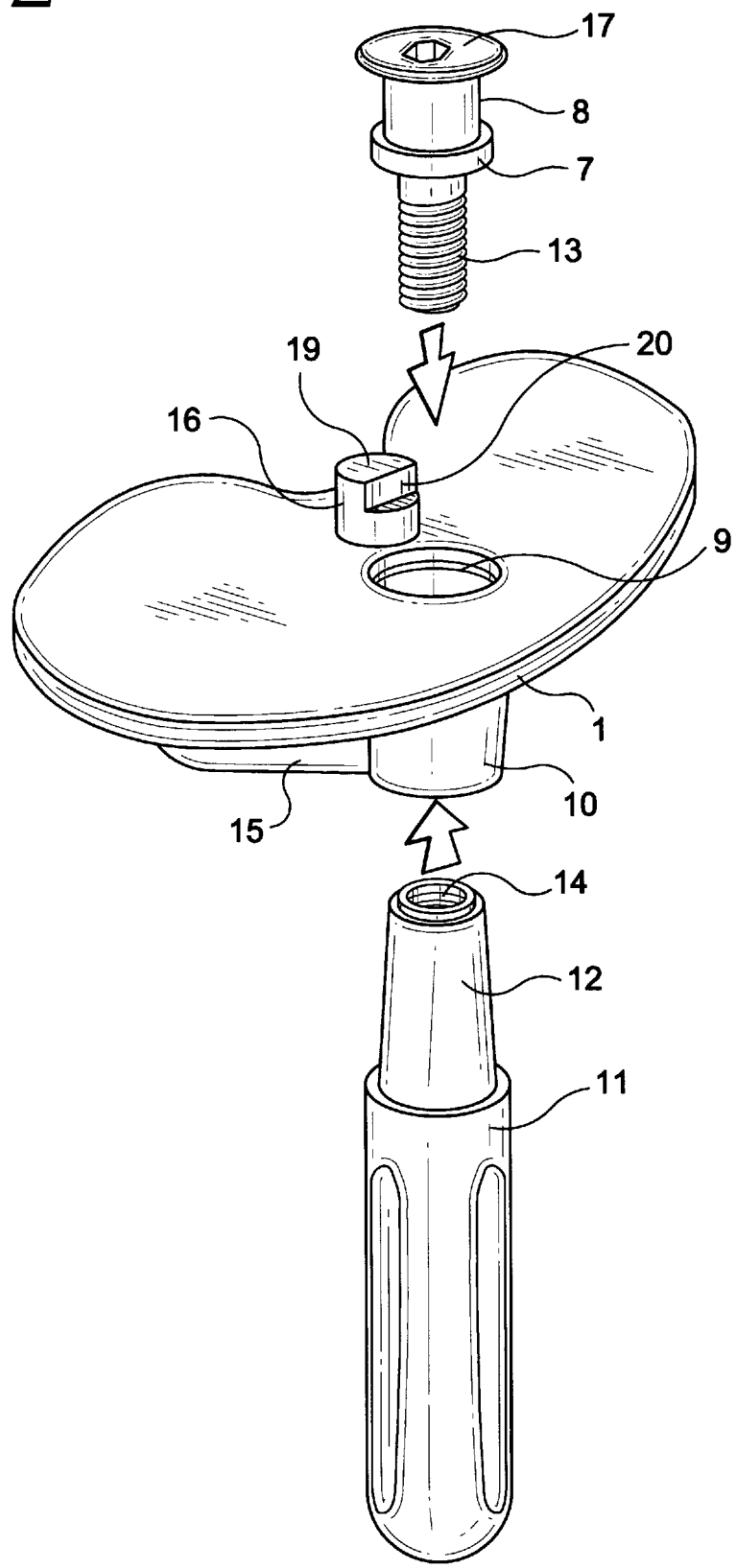
FIG. 2 is an exploded view of the construction shown in FIG. 1 with the bearing component removed.
Figure 4:
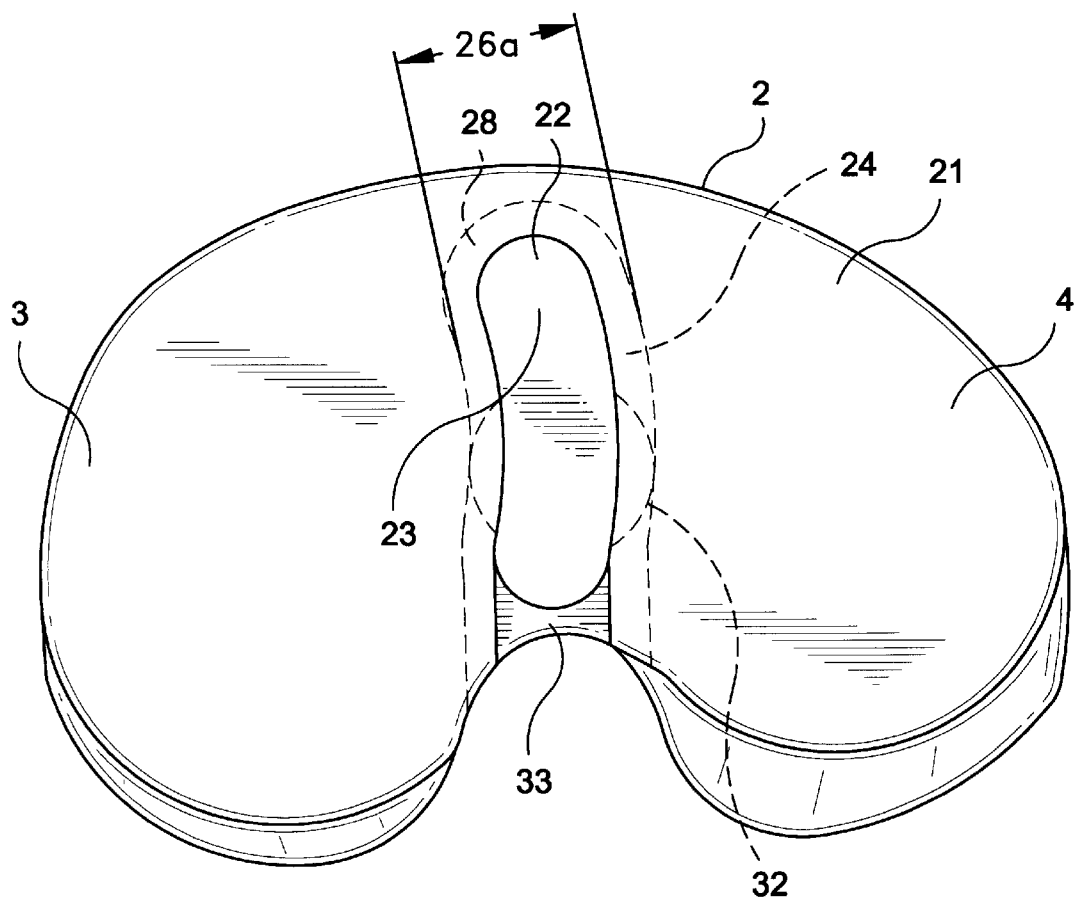
FIG. 4 is a plan view from below of the bearing component shown in FIG. 3.

As shown in FIGS. 1 and 2 a tibial element for a replacement knee prosthesis comprises a tibial tray 1 on which is carried a bearing component 2 having medial ad lateral compartments respectively 3 and 4 and which are best shown in FIG. 4. The upper surfaces of the compartments 3 and 4 are shaped to provide bearing surfaces 5 and 6. The tray itself is standard for both left and right knees and is substantially symmetrical about a vertical axis.

Fastening means are provided which act to secure an attachment element in the form of a stem to the lower part of the tray. These are in the form of a screw 7 having an enlarged boss shaped head 8. The lower part of the boss bears against a flange 9 on the tray and enters a tapered opening 10 where it acts to retain a stem 11 which has a cooperating tapered spigot 12 by engaging a screw thread 13 in a socket 14.

The lower surface of the tray can be provided with shaped engagement features 15 intended for engagement with the proximal sub-condylar area of the tibia of the patient and the general construction of the connection between the tray and the stem can, for example, be as set forth in the Applicant's European Patent Application 0 552 950 (H.42).

The upper surface of the tray 1 is provided with a central abutment 16, the function of which will be defined hereunder. It will be seen that the boss 8 of the screw 7 projects upwardly and the upper end is provided with a flange 17. When in position, the upper surface 18 of the boss 8 is substantially horizontally in line with the upper surface 19 of the abutment 16. As is most clearly shown in FIGS. 1 and 2, the side of the abutment 16 adjacent the boss 8 is cut away to provide a recess 20 within which the flange 17 of the boss 8 is located when the screw 7 is in position.

Figure 3:
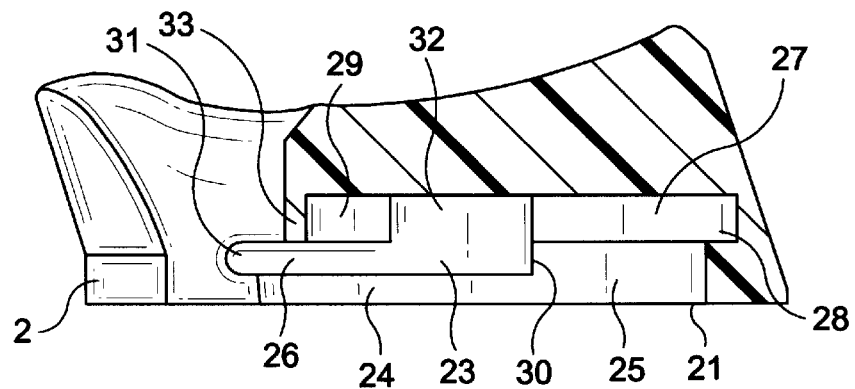
FIG. 3 is a cross-sectional side elevation of the bearing component shown in FIG. 1.

As shown in FIGS. 3 and 4, the bearing component 2 has medial 3 and lateral 4 compartments and can be made from any suitable bearing material, for example, ultra high molecular weight polyethylene. The lower surface 21 of the bearing component 2 is shape to provide a curved track 22 which is most clearly shown in FIG. 4. This curved track 22 is provided by a recess 23 that is formed with a peripheral inwardly protruding securing flange 24 around its edges. At the anterior end of the recess 23 the flange is deeper and is indicated by reference numeral 25.

Above the flange 24 the recess 23 is shaped to provide two horizontally extending grooves, the lower groove being indicated by reference numeral 26 and an upper groove 27 above the deeper portion 25 of the flange 24. The anterior end of the upper groove 27 is in the form of a radiused portion 28 so that the groove is closed at this end. The posterior end of the upper groove also has a radiused portion 29.

The posterior ends 31 of the lower groove 26 are open and emerge out of the side wall of the bearing component 2.

At this point where the lower posterior groove 26 meets the upper anterior groove 27 there is an enlargement provided by a circular vertically extending well 32, the diameter of which is equal to the horizontal distance extending between the base of the groove on either side of the recess 23.

The posterior end of the upper groove 27 is closed by a wall 33.

The horizontal distance between the base of the grooves 26 and 27 and indicated by arrows 26a is slightly more than the diameter of the flange 17 on the boss 8, the vertical depth of the lower posterior groove 26 is slightly greater than the vertical thickness of the flange 17 and the vertical depth of the upper anterior groove 27 is slightly greater again.

FIGS. 5 to 10 show how the bearing component 2 is placed in position and located on the tibial tray 1.

Figure 5:
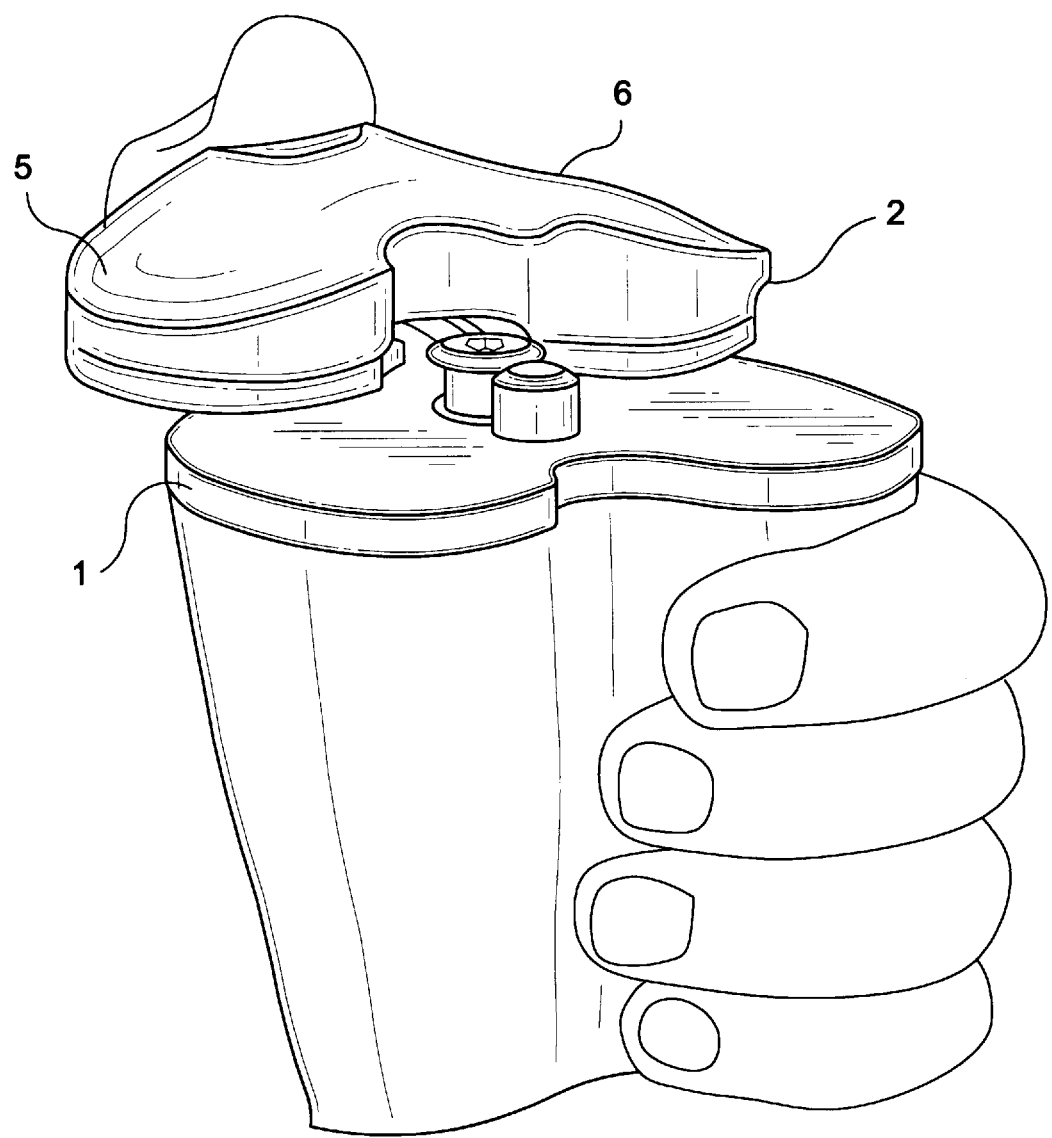
FIG. 5 is a diagrammatic representation showing how the bearing component is placed in position on the tibial tray.
Figure 6:
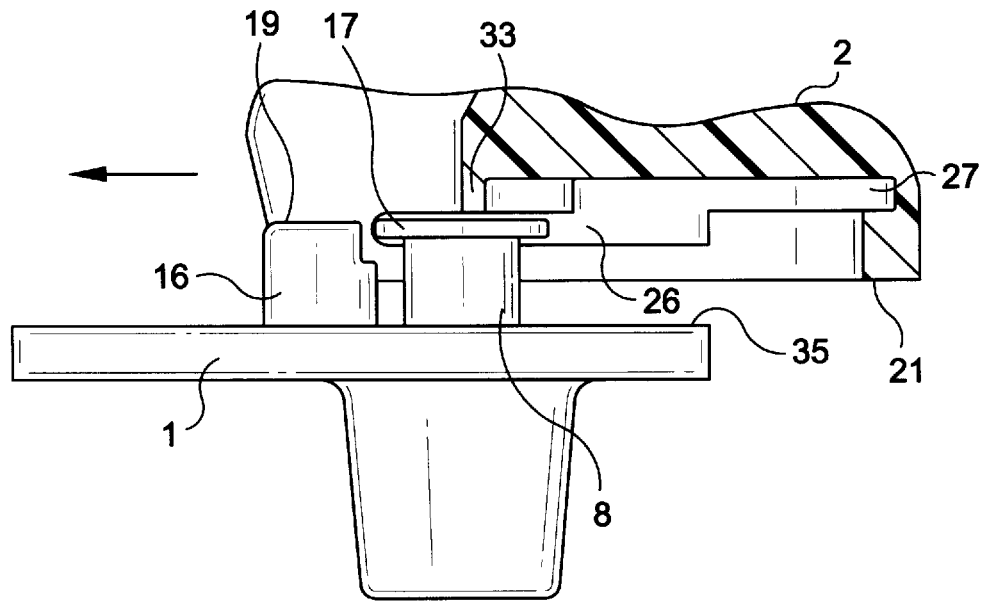
FIG. 6 is a part cross-sectional side view showing the bearing component in the position shown in FIG. 5 and about to be pushed into position.

In the position shown in FIGS. 5 and 6 the bearing component is inserted by pushing its posterior side towards the boss 8. At this position, as shown in FIG. 6, the lower surface 21 of the bearing component is raised above the upper surface 35 of the tray so that the open ends 31 of the lower posterior groove 26 engage over the flange 17 of the boss 8.

Figure 7:
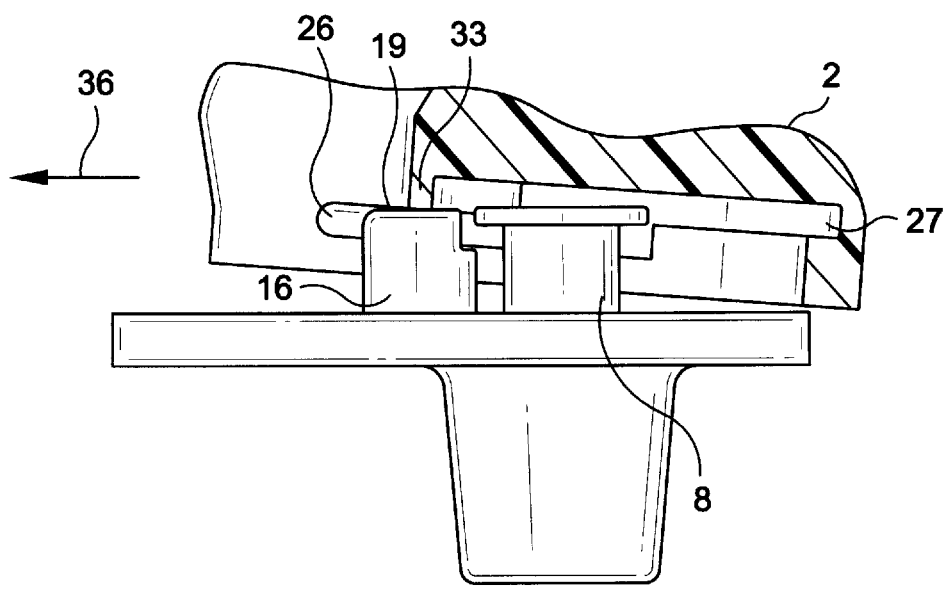
FIGS. 7 and 8 are views similar to FIG. 6 showing the bearing component in sequential loading positions of assembly.

Further movement in the direction of the arrow 36 in FIG. 7 shows that the bearing component 2 now has to be tipped to allow the flange 17 on the boss 8 to pass upwardly through the well 32 and into the upper anterior groove 27. The tipping movement is caused due to the upper surface 19 of the abutment 16 engaging the wall 33 at the end of the upper groove 28, and the flange 17 passing upwards in the well 32.

Figure 8:
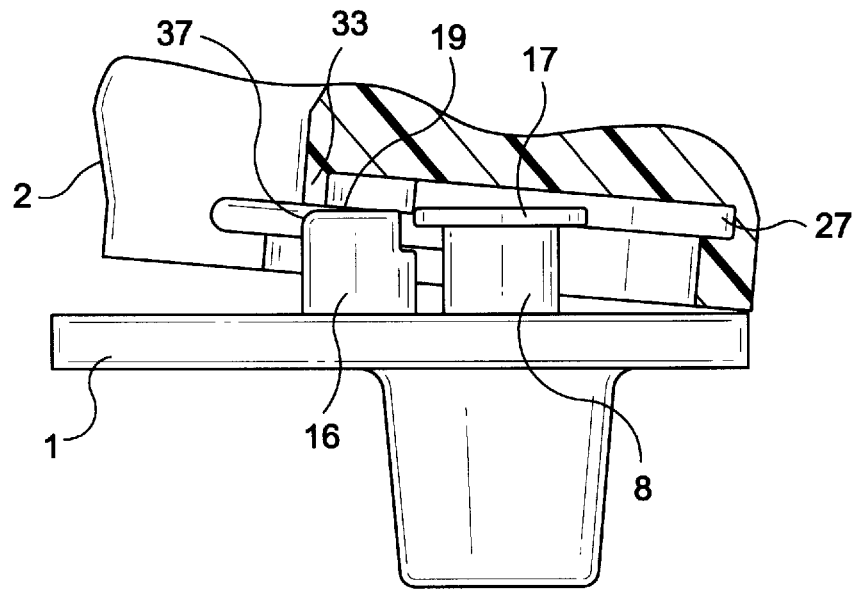

Further posterior movement achieves the position shown in FIG. 8 in which the anterior side of the flange 17 of the boss 8 has entered the upper groove 27 but the posterior corner 37 is still engaging the lower corner of the wall 33.

Figure 9:
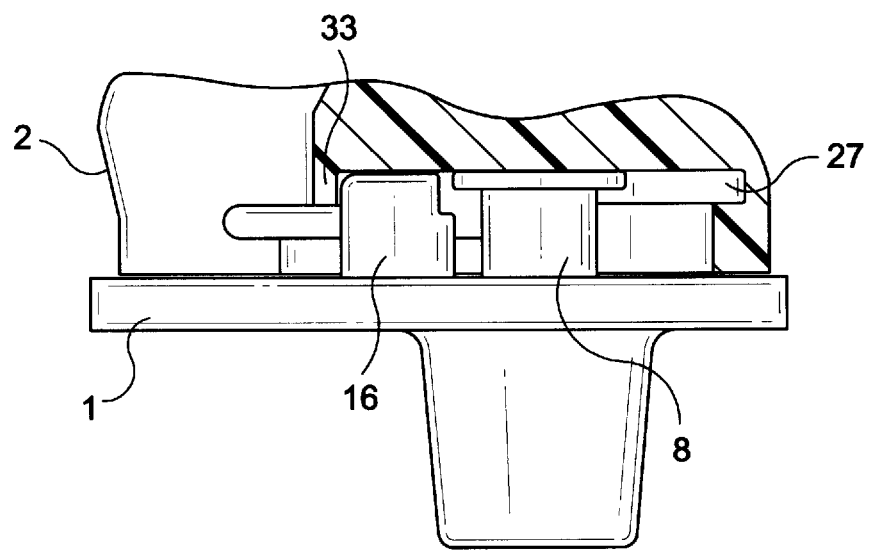
FIG. 9 is a view similar to FIG. 6 showing the bearing component after loading and in an anterior position.

Due to the resilient nature of the material from which the bearing component is made, UHMWPE, the bearing component can now be snapped downwards by resiliently deforming the end of the wall 33 over the corner 37 of the abutment 16 to the position shown in FIG. 9 where the bearing component is in its most anterior position. It will be seen that the abutment 16 now engages within the curved portion 29 at the posterior end of the upper groove 27 and the wall 33 prevents further anterior movement.

Figure 10:
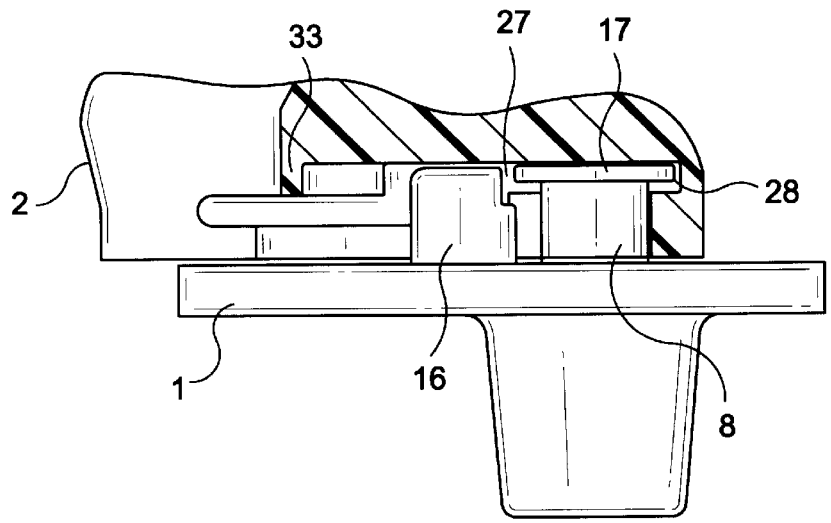
FIG. 10 is a view similar to FIG. 9 showing the bearing component after loading and in a posterior position.

The bearing component can, however, move in a posterior direction until the boss 8 engages the anterior end of the recess 23 as shown in FIG. 10. The flange 17 acting in the upper groove 27 prevents vertical removal of the bearing component and its horizontal movement on the tray 1 is controlled by the guide abutment 16 and boss 8 which are located in tandem in the curved track 22.

The boss 8 provides a guide and with its flange 17 provides independently operable means for securing the bearing to the tray, the bearing component being a resilient snap fit into the guide which can be releasable.

The abutment 16 and boss 8 which are in tandem together act as control means between the tray and the bearing component to allow free posterior and anterior movement of the lateral compartment 4 which is greater than the small amount of free posterior and anterior movement of the medial compartment 3 in relation to the tray 1.

Figure 11:
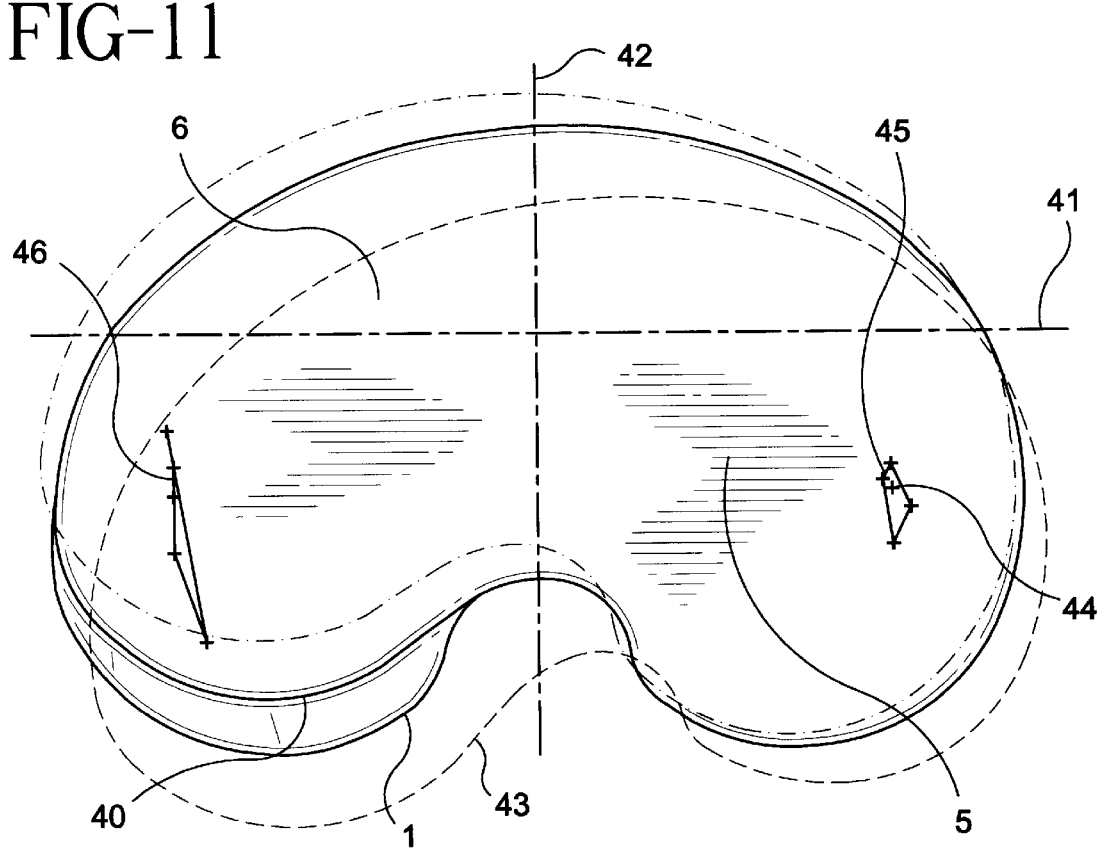
FIG. 11 is a diagrammatic plan view illustrating the range of movement of the bearing component on the tray.

FIG. 11 shows the relative movement. The central position of the bearing component 2 on the tray 1 is indicated by solid line 40. The general axes of the tray 1 are indicated by broken lines 41 and 42. From these it will be seen that in plan view the tray 1 is symmetrical about the center line 42 but the medial compartment 5 of the bearing component 2 is larger than the tibial compartment 6.

From this central position the maximum posterior movement of the bearing component is indicated by broken line 43 and it will be seen that the tibial compartment has rotated about a mobile axis 44, the locus of movement of which is indicated by the lines and crosses a45. The locus of movement of a similar point on the lateral compartment 6 is indicated by crosses and lines 46 and the much greater range of movement will be apparent.

If desired, the shape of the track 22 can be arranged so that there is virtually no relative free posterior movement and anterior movement of the medial compartment 5.

In the construction described and shown in the drawings, the control means acting between the tray 1 and the bearing compartment 2 allow rotational movement of the lateral compartment 6 in relation to the tray 1 about the pivotal axis 44 centered on the medial compartment and the arrangement allows restricted anterior and posterior movement of this pivotal axis.

It will be appreciated that other means for controlling the movement of the lateral compartment could be employed, for example, the control means could be in the form of a pivot which provides an axis of rotation and which would be centered on the medial compartment. Such a pivot could even allow a restricted free posterior and anterior movement relative to the tray.

Figure 12:
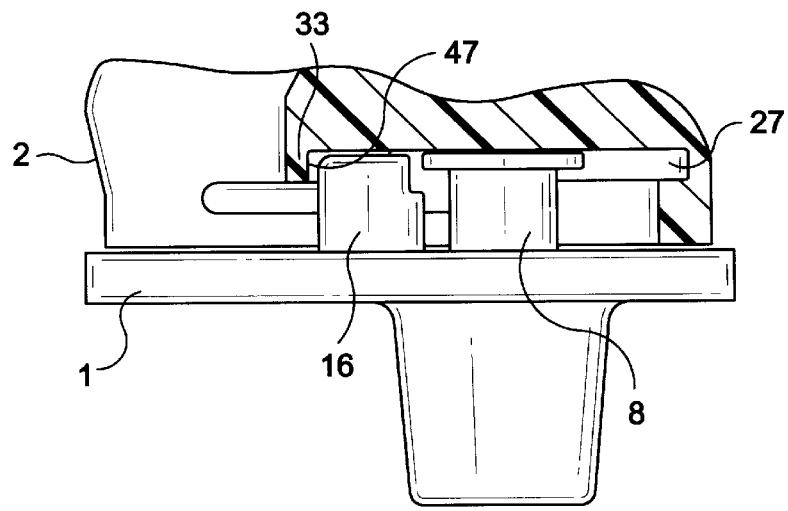
FIG. 12 is a view similar to FIG. 9 but showing a construction in which the bearing component is not removable.

FIG. 12 shows an alternate construction in which the bearing component 2 is not removable once it has been fitted. In this construction the abutment 16 is provided with a projecting lip 47 which can engage a cooperating lip 48 on the wall 33 to prevent the bearing component 2 from being tipped to allow the wall 33 to be resiliently deformed and sprung over the corner 37 of the abutment 16.

Figure 13:
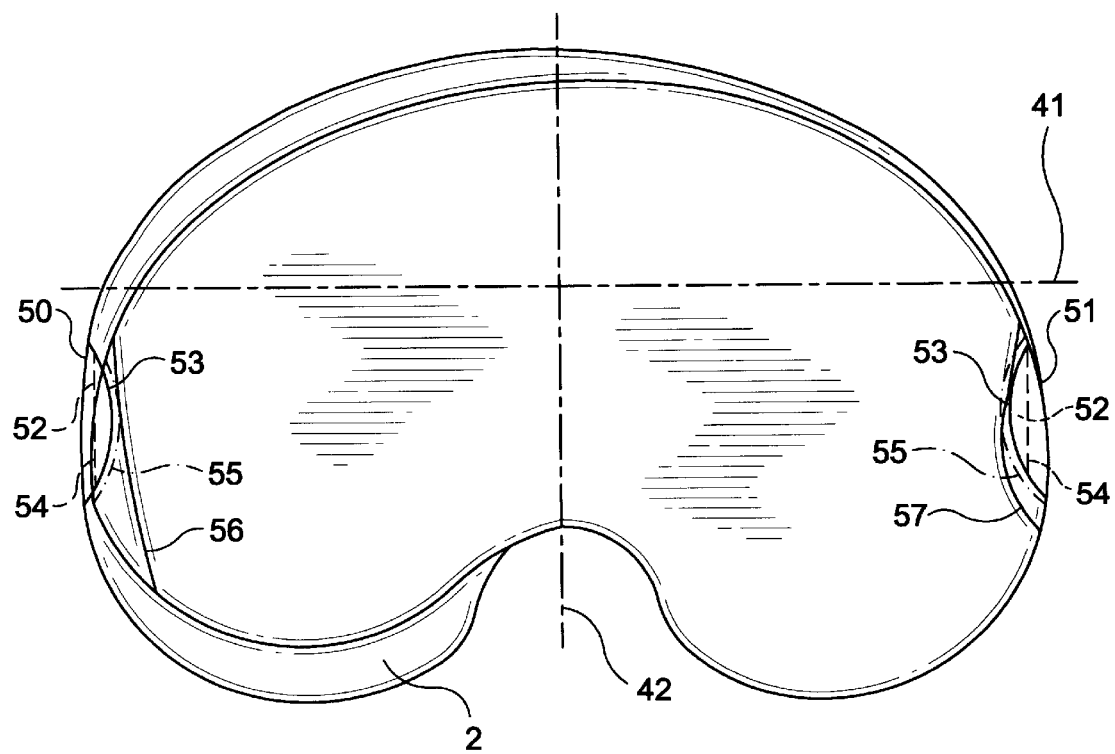
FIG. 13 is a diagrammatic plan view of the bearing component in position on the tibial tray and showing additional features which can be incorporated.

FIG. 13 shows a construction in which a multi functional tibial tray is employed and which can be used for a construction as described above and as shown in the drawings or with one in which the bearing component is fixed in position in relation to the tray 1.

With this construction medial and lateral retaining means are provided in the form of abutments 50 and 51. Each abutment comprises an upwardly projecting portion 52 and a horizontally projecting flange 53. The bearing component for use in a fixed construction has an outwardly projecting flange 54 enclosed in a cut out segment 55 indicated by broken lines. The construction is such that as the bearing component is snapped into position, the flanges 54 resiliently deform and pass below the flanges 53 so that the edges of each segment 55 locate the bearing component against posterior and anterior movement.

When such a tray is to be used with sliding meniscal component of the kind described herein and with reference to the drawings, the bearing component is cut away on each side along a line indicated by reference numerals 56 and 57 so that each relative movement between the tray and the bearing component is not impaired.

It will be appreciated that with the constructions described above in which the bearing component moves in relation to the tray that the bearing components have to be handed.

An advantage of the construction shown in the drawings is that if required, the bearing component can be removed from the tray by reversing the loading procedure and replaced without disturbing the tray or the connection to the stem. Again, the construction allows stems of different sizes and shapes to be used as required by the surgeon.

The invention, through the provision of the asymmetric bearing component and the capture, provides good postoperative stability of the joint, provides a low sensitivity to surgical technique and soft tissue quality and provides a mechanism to avoid the likelihood of bearing component dislocation and other bearing damage.

We claim:

1. A tibial element for a replacement knee prosthesis comprising a tibial tray having an upper surface provided with a bearing component having medial and lateral compartments, and including control means acting between said tray and said bearing component which provides free posterior and anterior movement of the bearing lateral compartment which is greater than any allowed free posterior and anterior movement of the bearing medial compartment in relation to the tray, said control means including a curved track in the base of the bearing component and a guide in the form of a projecting boss located within said track and carried on said tray, said guide provided by part of a fastener which acts to secure an attachment element to the lower part of the tray.

2. A tibial element for a replacement knee prosthesis as claimed in claim 1 in which said control means acting between said tray and said bearing component allows rotational movement of said lateral compartment in relation to said tray about a pivotal axis centered on said medial compartment.

3. A tibial element for a replacement knee prosthesis as claimed in claim 2 in which said control means also acts to allow restricted anterior and posterior movement of the pivotal axis.

4. A tibial element for a replacement knee prosthesis as claimed in claim 1 in which said tray is substantially symmetrical about a vertical axis.

5. A tibial element for a replacement knee prosthesis as claimed in claim 1 in which the medial compartment is larger than the tibial compartment.

6. A tibial element as claimed in any one of claim 1 in which the guide also provides means for securing the bearing component to the tray.

7. A tibial element for a replacement knee prosthesis as claimed in claim 1 in which said bearing component resiliently snaps onto the guide.

8. A tibial element as claimed in claim 1 in which said boss has a projecting flange shaped to engage a securing flange provided on the bearing component.

9. A tibial element as claimed in claim 8 in which two vertically spaced apart grooves are provided in the bearing component, the upper groove receiving said securing flange and the grooves being interconnected to allow the projecting flange on said boss to move between them.

10. A tibial element as claimed in claim 9 in which a control abutment is located posteriorly of said guide.

11. A tibial element as claimed in claim 9 in which said control abutment is integrally formed on said tibial tray.

12. A tibial element for a replacement knee prosthesis comprising:

a tibial tray having a first boss extending from an upper surface thereof and a boss extending upwardly from said upper surface located posteriorly of said first boss, said bosses having generally the same cross-sectional dimensions, said first boss having a flanged upper end;

a bearing component having a lower surface for engaging the upper surface of said tray, said lower surface having a curved track in the form of an open slot extending in the anterior-posterior direction, an internal flange in the form of a groove formed around the edges of said slot for receiving the flange of said first boss, said slot having a width generally corresponding to the cross-sectional dimension of said bosses, said groove having an anterior end recessed further from said lower surface than a posterior end of said groove, said groove having an enlarged opening between said anterior and posterior ends thereof for receiving said flanged upper end of said first boss allowing said flange to move from said posterior end of said groove into said recessed anterior end of said groove.

13. A tibial element as set forth in claim 12 wherein said tibial tray has a centrally located bore and said first boss has a threaded portion for engaging said bore to fixedly attach said first boss to said tray.

14. A tibial component as set forth in claim 13 wherein a modular stem having a threaded bore is coupled to an underside of said tibial tray by engagement between said threaded portion of said first boss and said threaded bore.

* * * * *

UNITED STATES PATENT AND TRADEMARK OFFICE
CERTIFICATE OF CORRRECTION

PATENT NO. : 5,879,394
DATED : March 9, 1999
INVENTOR(S) : Alan Ashby, et al.

It is certified that error appears in the above-identified patent and that said Letters Patent is hereby corrected as shown below:

On the title page, item [56] insert the following:

FOREIGN PATENT OR PUBLISHED FOREIGN PATENT APPLICATION

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | EP | 0 | 6 | 3 | 4 | 1 | 5 | 5 | 01-18-1995 | Europe | | | |
| | EP | 0 | 6 | 3 | 4 | 1 | 5 | 6 | 01-18-1995 | Europe | | | |

Signed and Sealed this

Second Day of November, 1999

Attest:

*Attesting Officer*

Q. TODD DICKINSON

*Acting Commissioner of Patents and Trademarks*

UNITED STATES PATENT AND TRADEMARK OFFICE
CERTIFICATE OF CORRECTION

PATENT NO.   : 5,879,394
DATED        : March 9, 1999
INVENTOR(S)  : Ashby et al.

It is certified that error appears in the above-identified patent and that said Letters Patent is hereby corrected as shown below:

Column 3, line 67, "shape" should read --shaped--.
Column 5, line 50, "multi functional" should read --multi-functional--.
Column 5, line 60, "cut out" should read --cut-out--.
Column 6, line 24, "provides" should read --provide--.
Column 6, line 41, "acts" should read --act--.
Column 6, line 50, cancel the words "any one of".
Column 6, line 60, "spaced apart" should read --spaced-apart--.

Signed and Sealed this

Fourteenth Day of November, 2000

Attest:

Q. TODD DICKINSON

*Attesting Officer*        *Director of Patents and Trademarks*